United States Patent [19]

Rellstab et al.

[11] 4,152,075

[45] May 1, 1979

[54] IMMERSIBLE PROBE FOR OPTICAL DUAL BEAM-MEASURING APPARATUS

[75] Inventors: Werner Rellstab, Steg; Jürg Daetwyler, Benglen, both of Switzerland

[73] Assignee: Mettler Instrumente AG, Greifensee-Zürich, Switzerland

[21] Appl. No.: 783,267

[22] Filed: Mar. 31, 1977

[30] Foreign Application Priority Data

Jun. 15, 1976 [CH] Switzerland .................. 7583/76

[51] Int. Cl.² .................................. G01N 21/22
[52] U.S. Cl. .................................. 356/435; 250/575; 250/227
[58] Field of Search .............. 356/206, 208; 250/227, 250/575

[56] References Cited

U.S. PATENT DOCUMENTS

| 2,324,304 | 7/1943 | Katzman | 356/208 |
| 3,384,885 | 5/1968 | Forbush | 356/72 X |
| 3,506,358 | 4/1970 | Baba et al. | 356/206 X |
| 3,851,976 | 12/1974 | Meier | 356/206 |

*Primary Examiner*—Vincent P. McGraw
*Attorney, Agent, or Firm*—Werner W. Kleeman

[57] ABSTRACT

An immersible probe for optical dual beam-measuring apparatus, comprising a sample feeler intended to be immersed in a sample for performing a measurement at the sample to be analyzed. The sample feeler is equipped with a light conductor. There is further provided a reference feeler immersible in a standard medium Both the sample feeler and the reference feeler are attached to a probe body.

2 Claims, 1 Drawing Figure

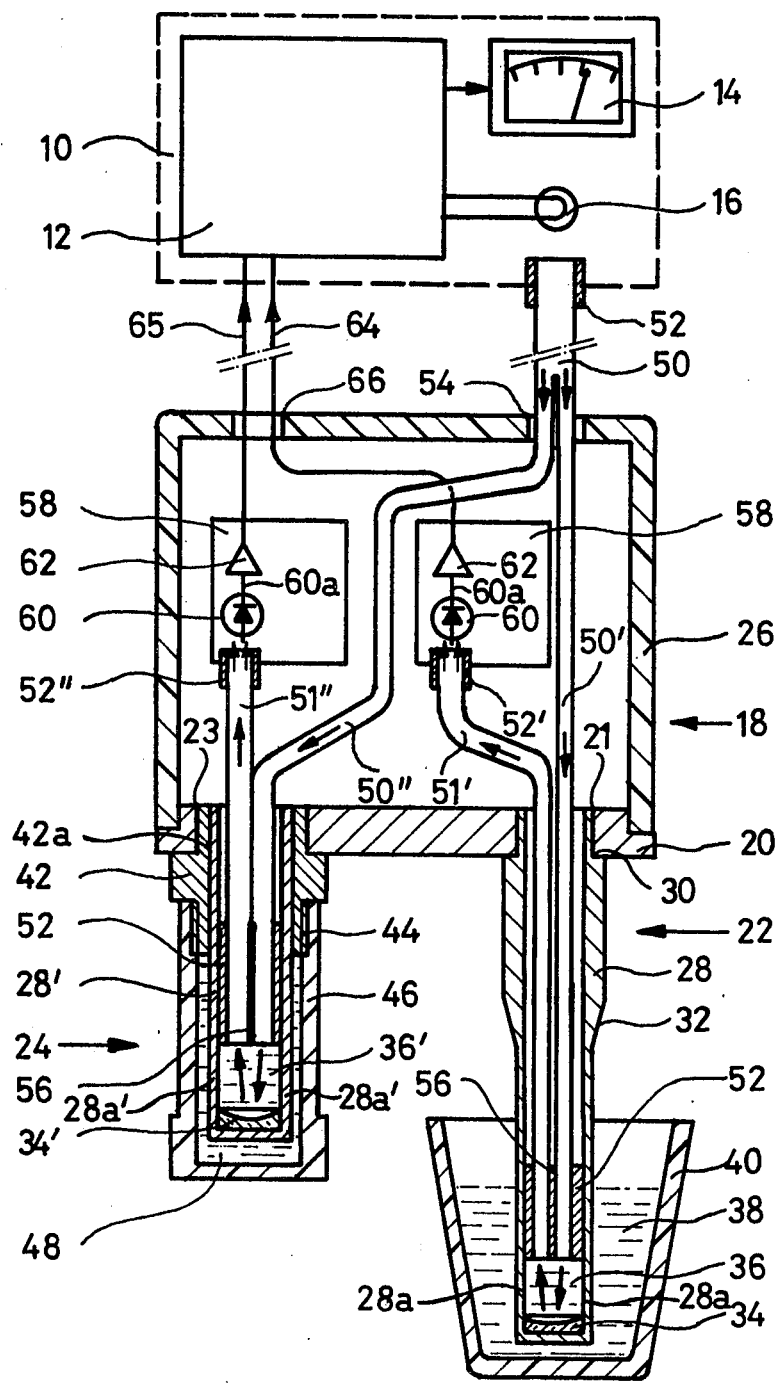

IMMERSIBLE PROBE FOR OPTICAL DUAL BEAM-MEASURING APPARATUS

BACKGROUND OF THE INVENTION

The present invention relates to a new and improved construction of an immersible probe for optical dual beam-measuring apparatus, which is of the type comprising a sample feeler intended to be immersed in a sample to be analyzed and for carrying out a measurement thereat, the sample feeler being equipped with a light conductor.

Equipment of this general type is used in photometry, turbidimetry and for the performance of photo titrations. As a general rule the analysis is carried out while working with liquid samples.

In order to obtain satisfactorily accurate and reproducible measurement results when working with dual beam-measuring apparatuses the measurement signal is compared with a reference signal and the relationship of both signals to one another is evaluated. With a state-of-the-art arrangement the reference signal is directly derived from the common light source. With this technique it is only possible to eliminate instabilities of the light source as a possible source of error adversely effecting the measurement result. However, such type of arrangement can only be designated with qualification as a dual beam-measuring apparatus. True dual beam-measuring apparatuses of the prior art are classified as that type of equipment where the light penetrates through both a sample cuvette and a reference cuvette. Apart from errors attributable to the light source it is then also possible to compensate such predicated, for instance, upon the nature and properties of the solvent which is employed.

With analysis equipment utilizing immersible probes additional errors exist which typically result from the light path both leading to and from the sample sensor, which light paths normally are quite long.

Furthermore, it is in principle advantageous and desirable to carry out to the extent possible a separation of the "wet" part (sample and standard or reference medium) and "dry" part (control component), and furthermore, to design the equipment such that handling of the standard or reference medium is simple.

SUMMARY OF THE INVENTION

Therefore, with the foregoing in mind it is a primary object of the present invention to provide a new and improved construction of immersible probe for optical dual beam-measuring apparatus which effectively satisfies the aforementioned requirements.

Another object of the present invention is concerned with a novel construction of immersible probe for use with an optical dual beam-measuring apparatus which minimizes the occurrence of possible errors attributable to the light paths.

Another and more specific object of the present invention is concerned with the provision of a new and improved construction of immersible probe which, with appropriate design of the measuring portion and reference portion of the system allows achievement of more accurate and better reproducible measurements as well as also simplier handling of the equipment.

Now in order to implement these and still further objects of the invention, which will become more readily apparent as the description proceeds, the immersible probe of this development utilizes a reference feeler immersible in a standard or reference medium. Both the sample feeler and such reference feeler are attached to a probe body. With this design it is possible to configure practically identically the light paths of the measuring portion as well as also the reference portion of the equipment, so that in both branches of the system there prevail approximately the same errors i.e. losses attributable to the length of the respective light paths and the number and nature of the transitions to which the light is subjected as it moves through such light paths.

Hence, while the reference feeler is preferably structured to be shorter than the sample feeler, the reference feeler nonetheless extends essentially in the same direction as the sample feeler. With this construction there can be obtained the beneficial result that also the reference feeler is located at the direct neighborhood of the sample, so that there is also reduced, for instance, possible temperature influences upon the measurement result. The difference between the respective lengths of the sample feeler and reference feeler becomes of lesser significance the greater the total length of the light conductor.

Typically, the standard or reference medium (as well as also the sample medium) is a liquid. Therefore, for the reception and housing of the standard or reference medium there is provided a reference vessel which can be threadably connected with the probe body. This construction allows a particularly simple and rapid exchange of the standard or reference liquid in order to modify the equipment for working with a different type of sample or for carrying out a different measurement function. Apart from these benefits, there also exists the possibility of providing for the same measuring apparatus or control portion or part of the system a number of exchangeable probe bodies, each containing a different standard or reference liquid.

The probe body advantageously contains a respective opto-electrical transducer for the sample feeler and the reference feeler, respectively. Consequently, the total light path also then can be appreciably shortened if the light source is arranged in the control portion of the equipment. It is further advantageous to connect in circuit at the output side of each transducer an amplifier in the probe body. Due to amplification of the measuring signal and reference signal at a point near the measuring location, it is possible to reduce the influence of electrical disturbance or spurious signals even with relatively large spacing of the measuring or measurement location from the control portion. There is thus obtained better signal output.

BRIEF DESCRIPTION OF THE DRAWING

The invention will be better understood and objects other than those set forth above, will become apparent when consideration is given to the following detailed description thereof. Such description makes reference to the annexed drawing wherein the single FIGURE schematically illustrates an optical dual beam-measuring apparatus, showing in sectional view details of the immersible probe constructed according to the invention.

DETAILED DESCRIPTION OF THE PREFERRED EMBODIMENTS

Turning attention now to the drawing, it is to be understood that in order to simplify the illustration only enough of the dual beam-measuring apparatus has been shown therein to enable those skilled in the art to readily understand the underlying principles and concepts of the invention, which is particularly concerned with the novel construction of immersible probe useful in conjunction with such type measuring apparatus. Therefore, the control portion 10 of the equipment has only been schematically indicated since the invention is not concerned with any specific type of control and the details thereof are unnecessary for understanding the teachings related to the immersible probe. This control portion 10 typcially contains the electrical circuitry 12 for the power supply as well as signal amplification and evaluation. As such type circuitry is conventional in this art and the details thereof are not crucial to the understanding of the invention, it is to be understood that a conventional circuitry suitable for the purposes of the invention may be employed. Further, the control portion 10 will be seen to contain a suitable display device 14 and also is equipped with a light source 16. A particularly simple type of light source 16 which may be used is an incandescent lamp, but however more frequently there is used in conventional manner, for instance, a monochromatic light transmitter.

As mentioned, the invention is concerned with details of an immersible probe which can be especially used in the environment of a dual beam-measuring apparatus incorporating a standard control portion 10 as above indicated. This immersible probe has been generally indicated in the drawing by reference character 18 and will be seen to comprise a base or floor portion 20 having the openings 21 and 23 formed conveniently thereat for the attachment therewith of a sample feeler 22 and a reference feeler 24. A cover 26, which may be formed of plastic or any other suitable material, provides a housing for the probe body 18 and is fixed in any convenient fashion to the base portion 20.

As to the sample feeler 22 the same will be seen to comprise a sleeve or sleeve member 28 having a stepped shoulder 30 at its upper end which is inserted into its related opening 21. Approximately at one-half of the length of the sleeve 28 the same is constricted to provide a tapered portion or tapering 32 facilitating insertion into a not particularly illustrated holder having a standard ground opening. At the lower, closed end of the sleeve 28 there is inserted a concave reflector 34. Lateral openings 28a provided at the lower end or region of the sleeve 28 form a chamber 36 dispositioned above the concave reflector 34. This chamber 36 is filled with the sample liquid 38 when the sample feeler 22 is immersed therein. For confining the sample liquid 38 there can be provided a beaker 40 or other equivalent receptacle.

The reference feeler 24 similarly comprises a sleeve or sleeve member 28'. This sleeve 28' is inserted into a bore 42a of an intermediate bushing 42 which, in turn, is conveniently fixed in its related opening 23 provided at the base portion 20. At the lower end of the reference feeler 24 there is likewise inserted a concave reflecter 34', and here also lateral openings, generally indicated by reference character 28a', of the sleeve 28', form a chamber 36'. The intermediate bushing or sleeve 42 is equipped with external threading 44, to which there can be threadably connected a vessel 46 or equivalent structure which is filled with the standard or reference liquid.

The light source 16 illuminates a flexible light conductor or light conductor means 50 formed of bundled optical glass fibers which are retained together at their ends confronting the light source 16 by means of a metallic sleeve 52. The light conductor 50 is surrounded by a not particularly illustrated flexible hose or covering and can be inserted by any suitable coupling connection into the control portion 10. Further, light conductor 50 is guided through an opening 54 of the cover 26 into the interior of the probe body 18. Immediately after entering the hollow probe body 18 this light conductor 50 divides into two branches, one of which defines a sample branch 50' and the other a reference branch 50". Both of the branches 50' and 50" are extended almost to the end of the related sample feeler 22 and reference feeler 24 respectively. At that location each of both branches 50' and 50" of the light conductor 50 is connected by means of a respective metal sleeve 52 with a respective further light conducting branch 51' and 51". Both of the respective branch pairs 50', 51' and 50", 51" are separated at the region of the associated sleeve 52 by a light pervious wall 56 in such a manner that there are formed semicircular-shaped boundary surfaces or interfaces between the light conductor and medium.

The ends of the bundle of optical glass fibers forming the branches 51' and 51", which are held together by the sleeves 52' and 52" respectively, or equivalent structure, each extend into a small cabinet or box 58. Arranged beneath each of the two ends of the branches 51' and 51" is a respective photodiode 60, the signals of which appearing at the respective diode output 60a, after being delivered through a respective associated pre-amplifier 62 connected at the output side of the related diode, are delivered by means of the lines or conductors 64 and 65 extending through an opening 66 and the cover 26, to the control portion or part 10 of the equipment. Both of the cabinets or boxes 58 are threadably connected by suitable spacer elements with the base or base portion 20 of the probe body 18.

From the foregoing description it will be apparent that the path of the light beams or rays thus leads from the light source 16 through the light conductor 50, and, in the case of the sample feeler 15, through the branch 50', the chamber 36, the reflector 34, the chamber 36 and the branch 51' to the associated photodiode 60, whereas, in the case of the reference feeler 24, via the branch 50", the chamber 36', the reflector 34', the chamber 36' and the branch 51', to the corresponding photodiode 60. In consideration of the fact that the length of the light conductor 50 between the control portion 10 and the sample body 18 can readily amount to 1 meter and more, it will be apparent that the light path and deflectional losses at both light paths are at least approximately the same, thus, the measurement result no longer can be falsified. By employing both of the pre-amplifiers 62 there is furthermore achieved the result that sufficiently powerful, distrubance-free electrical signals reach the control portion 10 of the equipment.

While there are shown and described present preferred embodiments of the invention, it is to be distinctly understood that the invention is not limited thereto, but may be otherwise variously embodied and practiced within the scope of the following claims.

Accordingly, what we claim is:

1. An immersible probe for an optical dual beam-measuring apparatus, comprising:
   a sample feeler capable of being immersed in a sample for analysis of such sample;
   a reference sensor capable of being immersed in a reference medium;

a probe body to which there are affixed both said sample sensor and said reference sensor;

light conductor means provided for said sample sensor and said reference sensor;

said reference sensor is structured to be shorter than said sample sensor;

both of said sensors extending essentially in the same direction;

a reference vessel for housing the reference medium;

screw means for releasably attaching said reference vessel to said probe body; and a respective opto-electrical transducer contained in said probe body and provided for each said sample sensor and reference sensor.

2. The immersible probe as defined in claim 1, wherein:

the reference vessel and the sample sensor are positioned parallel to each other.

* * * * *